(12) United States Patent
Pan et al.

(10) Patent No.: US 12,257,289 B2
(45) Date of Patent: Mar. 25, 2025

(54) SELF-ASSEMBLING OXYGEN CARRIER COMPOSITIONS

(71) Applicant: KaloCyte, Inc., Baltimore, MD (US)

(72) Inventors: Dipanjan Pan, Ellicot City, MD (US); Allan Doctor, Towson, MD (US); Philip C. Spinella, Chesterfiled, MO (US)

(73) Assignee: KaloCyte, Inc., Baltimore, MD (US)

( * ) Notice: Subject to any disclaimer, the term of this patent is extended or adjusted under 35 U.S.C. 154(b) by 186 days.

(21) Appl. No.: 17/238,809

(22) Filed: Apr. 23, 2021

(65) Prior Publication Data

US 2021/0330754 A1    Oct. 28, 2021

Related U.S. Application Data

(60) Provisional application No. 63/014,665, filed on Apr. 23, 2020.

(51) Int. Cl.

| | | |
|---|---|---|
| *A61K 38/42* | (2006.01) | |
| *A61K 9/127* | (2006.01) | |
| *A61K 9/1277* | (2025.01) | |
| *A61K 9/19* | (2006.01) | |
| *A61K 47/24* | (2006.01) | |
| *A61K 47/28* | (2006.01) | |
| *C07F 9/10* | (2006.01) | |

(52) U.S. Cl.
CPC ............ *A61K 38/42* (2013.01); *A61K 9/1277* (2013.01); *A61K 9/19* (2013.01); *A61K 47/24* (2013.01); *A61K 47/28* (2013.01); *C07F 9/10* (2013.01)

(58) Field of Classification Search
CPC ........ A61K 38/42; A61K 9/1277; A61K 9/19; A61K 47/24; A61K 47/28; A61K 9/08; A61K 9/127; C07F 9/10; C07F 9/106
See application file for complete search history.

(56) References Cited

U.S. PATENT DOCUMENTS

| | | | |
|---|---|---|---|
| 6,284,267 B1 | 9/2001 | Aneja | |
| 2006/0088583 A1* | 4/2006 | Takeoka | ............... A61K 9/0026 514/567 |
| 2009/0292019 A1* | 11/2009 | Fortin | ..................... C07F 9/091 554/224 |
| 2010/0094020 A1 | 4/2010 | Dewa et al. | |
| 2013/0345117 A1* | 12/2013 | Van Nieuwenhze | .... C07K 7/08 530/331 |
| 2016/0051635 A1* | 2/2016 | Lanza | ..................... A61K 9/107 424/497 |

FOREIGN PATENT DOCUMENTS

| | | | |
|---|---|---|---|
| JP | S62 94 A | 1/1987 | |
| WO | WO-2010144629 A1 * | 12/2010 | ............. A61K 38/17 |
| WO | 2012/073245 A1 | 6/2012 | |
| WO | 2012/108990 A2 | 8/2012 | |
| WO | 2013/032643 A3 | 3/2013 | |
| WO | 2015/069699 A1 | 5/2015 | |
| WO | 2018/160876 A1 | 9/2018 | |
| WO | 2021/217010 A1 | 10/2021 | |

OTHER PUBLICATIONS

International Search Report issued in copending Patent Application No. PCT/US21/28854 on Jul. 20, 2021.
Farzaneh S. Roodsari, "A New Approach to the Stereospecific Synthesis of Phospholipids. The Use of L-Glyceric Acid for the Preparation of Diacylglycerols, Phosphatidylcholines, and Relate Derivatives", Department of Chemistry, California State University (Mar. 1999), pp. 1-11.
Ram A. Vishwakarma, "New fluorescent probes reveal that flippase-mediated flip-flop of phosphatidylinositol across the endoplasmic reticulum membrane does not depend on the stereochrmistry of the lipid", Organic & Biomolecular Chemistry journal (Jan. 2005), pp. 1-10.
European Search Report issued in copending Patent Application No. 21793256.5 on Jun. 11, 2024.
Jarod Waybright, "Required hydrophobicity of fluorescent reporters for phosphatidylinositol family of lipid enzymes" National Institutes of Health (Jul. 2017), pp. 1-9.

* cited by examiner

*Primary Examiner* — David J Blanchard
*Assistant Examiner* — Edwin Coleman Mitchell
(74) *Attorney, Agent, or Firm* — Whiteford, Taylor & Preston, LLP; Peter J. Davis

(57) ABSTRACT

Synthetic blood substitutes and methods for making them. A lipid-amphiphile blood-substitute precursor compound having a hydrophobic fatty acid/acyl moiety, a hydrophilic head moiety including a phosphate group, and a pH responsive moiety. The lipid-amphiphile precursor is configured to self-assemble from a solution mixture of phospholipid and cholesterol in the presence of hemoglobin and an allosteric effector into a hybrid-vesicle resulting from the combined self-assembly of both the amphiphilic lipid-oligomer and the lipids into an advanced vesicular structure containing a hemoglobin/allosteric effector payload.

9 Claims, 9 Drawing Sheets

| Date | EM batch | Free Hb | Purification method |
|---|---|---|---|
| Apr-May.2019 | EM 2.1.2.2.019-022 | 36%-52% | TFF |
| Oct-Nov.2019 | EM 2.1.2.2.026-027 | 30%-35% | N/A |
| Nov.2019 | EM 2.1.2.2.028 | 11% | Dialysis |
| Dec.2019-Jan.2020 | EM 2.1.2.2.029-033 | 4%-20% | Dynamic dialysis |
| Jan-Mar.2020 | EM 2.1.2.2.034-037 | 3%-7% | N/A |
| Mar.2020 | EM 2.1.2.2.038 | 2.1% | Zn-Sepharose |

FIG. 4

| | Before lyophilization | Reconstitution (4 d) | Reconstitution (14 d) |
|---|---|---|---|
| Size | 131.1±69.8nm | 142.5±84.5nm | 161.8±94.6nm |
| Particle conc | 7.9E+11/mL | 5.6E+11/mL | 5.7E+11/mL |
| Zeta potential | -24.03±0.28mV | -24.32±0.42mV | -18.09±0.22mV |
| Free Hb | 7.76% | 10.10% | 10.83% (1), 7.89% (2) |

FIG. 9

SELF-ASSEMBLING OXYGEN CARRIER COMPOSITIONS

BACKGROUND OF THE INVENTION

Field of the Invention

The present invention relates to synthetic blood substitutes and/or oxygen carrier compositions and methods for making them.

SUMMARY OF THE INVENTION

The inventions described herein relate to synthetic blood substitutes and methods for making them. More specifically, the present invention is directed to a lipid-amphiphile blood-substitute precursor compound having a hydrophobic fatty acid/acyl moiety, a hydrophilic head moiety including a phosphate group, and a pH responsive moiety.

According to another embodiment of the invention, there is presented a composition including phospholipid-cholesterol solution, a lipid-amphiphilic precursor compound, hemoglobin, and an allosteric precursor.

According to a further embodiment of the invention, the lipid-amphiphile precursor is configured to self-assemble from a solution mixture of phospholipid and cholesterol in the presence of hemoglobin and an allosteric effector into a hybrid-vesicle resulting from the combined self-assembly of both the amphiphilic lipid-oligomer and the lipids into an advanced vesicular structure containing a hemoglobin/allosteric effector payload. According to a preferred embodiment, the structure is a hybrid vesicle having a diameter of about 80 nm to about 300 nm with an outer layer comprising a bilayer of amphiphilic precursor, cholesterol and polyethylene glycol-phosphatidylethanolamine ("PEG-PE") and having a payload comprising hemoglobin, allosteric effector and, optionally, a reducing agent, such as leucomethylene blue, n-benzoyl-leucomethylene blue, or methylene blue. The result is a novel synthetic blood substitute having net negative zeta potential, excellent payload retention and differential gas permeability. Moreover, unlike phospholipid bilayers in liposomal-based HBOCs, the synthetic blood substitute of the invention has a tunable membrane (in which different oligomeric amine moieties may be used in the precursor to vary the thickness of the membrane) offering greater integrity due to counter-ionic hemoglobin-precursor interaction and pH responsiveness.

According to a preferred embodiment, the phospholipids may be $PEG_{2000}$-PE (20 mol %), the ratio of phospholipid to cholesterol is preferably 17.00:2.34, and the allosteric effector may be RSR-13 (efaproxiral) present in a ratio to hemoglobin of 20:1 to 0.1:1, preferably 10:1:1 to 1:1, and most preferably 5:1. The lipid-amphiphile-precursor compound may be the compound represented by the following formula:

Formula I:

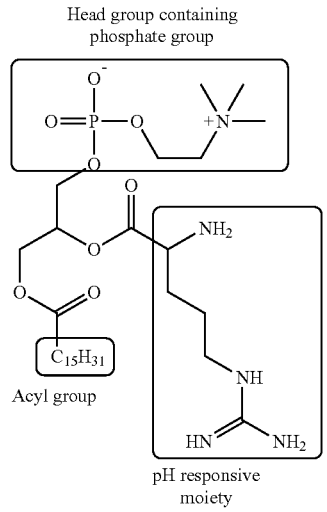

According to various alternative embodiments, the pH responsive moiety is preferably an amine, particularly tertiary amines, due to their feasibility to finely tune their pKa and since they can present a marginally lower pKa when substituted with longer hydrophobic chains. Tunable pKa can be achieved based on hydrophobic modification of the amines, whereas, increase of the hydrophobicity of the alkyl substituents will result in the linear decrease of pKa. The high abundance of the positive charges in the self-assembled vesical structure creates a unique charge density that drives the pH shuttle associated with hemoglobin uptake of oxygen at higher pH and the shedding of oxygen at lower pH.

Examples of suitable pH responsive moieties according to the invention include chitosan, lysine, ethyleneimine, ester amines, 2-(dimethylamino)ethyl methacrylate, amidoamine, arginine, spermine, spermidine, dimethylethanolamine, urethane, oxylysine, aminoglycolic acid, oxazoline, acrylamide, quaternium-6, piperidine, pyrrolidine, diphenylalanine, 1-adamantyl (5-bromo-2-methoxybenzyl) amine, ornithine, 2-(diisopropylamino)ethyl methacrylate, 4-vinyl pyridine, histidine, β-amino esters.

According to various other embodiments of the invention, the acyl moiety of the lipid amphiphile precursor may constitute the connection between the hydrophobic fatty acid moiety, the hydrophilic head moiety containing the phosphate group and the pH responsive moiety. According to these embodiments, the pH responsive moiety may be linked to, for example, a phosphoglyceride, including phosphatidyl choline, phosphatidyl ethanolamine, phosphatidyl inositol, phosphatidyl serine, lysophosphatidylcholine. The pH responsive moiety may be linked to either the sn1 (more preferred) or sn2 position of a phosphoglyceride. The preferred acyl chain length is 16-18, and the preferred ratio of acyl carbon chain and amine carbon chain would be between 16:4 and 18:6.

Therefore, the lipid-amphiphile-precursor according to the invention may have one of the formulas:

Formulas I and II:

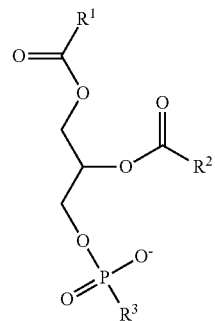
(I)

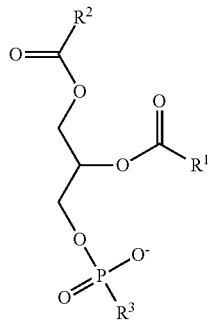
(II)

or a salts or tautomers thereof, wherein:
$R^1$ is a hydrophobic group;
$R^2$ is an amine containing group; and
$R^3$ is chosen from

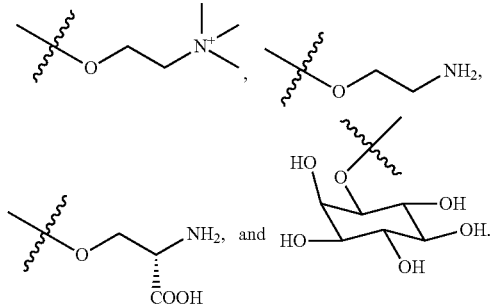

According to various embodiments, $R^1$ is alkyl, and is optionally substituted with one or more $R^4$; where each $R^4$ is independently chosen from alkyl and halo. According to various preferred embodiments, $R^1$ is $(CH_2)_l CH_3$; where l is an integer between 10 and 16, inclusive.

According to various embodiments, $R^2$ is $(CHR^5)_m R^6$ or $(CHR^5)_m NR^7 (CH_2)_n R^6$; where each $R^5$ is independently chosen from H and $N(R^7)_2$; at most one $R^5$ is not H; $R^6$ is chosen from $N(R^8)_2$ and $N=C(NHR^8)_2$; each $R^7$ is independently chosen from H and alkyl; each $R^8$ is chosen from H and alkyl; m is an integer between 2 and 6, inclusive; and n is an integer between 2 and 6, inclusive.

According to various embodiments $R^2$ is $CHR^5(CH_2)_o R^6$ or $CHR^5(CHR^5)_o NR^7 (CH_2)_p R^6$; and each $R^5$ is independently chosen from H and $N(R^7)_2$; at most one $R^5$ is not H; $R^6$ is chosen from $N(R^8)_2$ and $N=C(NHR^8)_2$; each $R^7$ is independently chosen from H and alkyl; each $R^8$ is chosen from H and alkyl; p is an integer between 2 and 6, inclusive; and o is an integer between 1 and 5, inclusive.

According to various embodiments, $R^3$ is chosen from

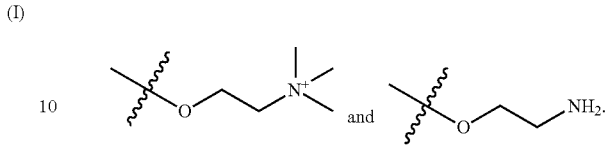

According to various embodiments, $R^3$ is

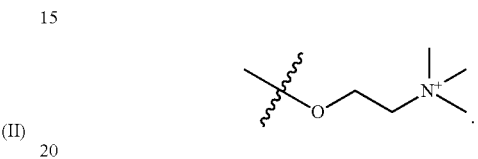

According to further aspects of the invention, the allosteric effector may be one or more of 2,3-DPG, RSR-13, inositol phosphate, inositol hexaphosphate (IP6), phytic acid, guanosine triphosphate.

According to still further embodiments of the invention, the phospholipid solution is most preferably a mixture of cholesterol and $PEG_{2000}$-PE in a ration of 17.00:2.34. According to alternative embodiments, the phospholipid solution may be PEG having molecular weights from 500 Da to 5000 Da in the event a lower or higher membrane thickness of the self-assembled particle is desired.

According to further embodiments of the invention, the synthetic blood substitute of the invention may be made by dissolving lipid-oligomeric amphiphile in a solution of phospholipid, followed by evaporation of the phospholipid to form a film. Frozen hemoglobin premixed with allosteric effector is thawed and transferred to the dried film and then mixed. After mixing of hemoglobin payload and membrane components, the mixture is sonicated and then allowed to rest to achieve equilibrium, followed by hydrodynamic diameter measurement of the self-assembled oxygen carrier particle. The mixture is then filtered until outlet flow is clear, and the hydrodynamic diameter is checked again.

According to further embodiments of the invention, following self-assembly of the lipid-amphiphile precursor and hemoglobin into the synthetic blood substitute of the invention, the resulting product is lyophilized for packaging. The lyophilized product is a powder comprising amphiphilic precursor, cholesterol and PEG-PE hemoglobin and allosteric effector, optionally also including cryoprotectants.

Reconstitution at the original EM production concentration (or concentrated) can be achieved with PBS/water by simple mixing and gentle vortexing/agitation.

BRIEF DESCRIPTION OF THE DRAWINGS

FIG. 4 is a table showing free hemoglobin detected following purification of batches of oxygen carrier particles using different purification methods.

FIG. 9 shows various properties of an oxygen carrier particle according to an embodiment of the invention before lyophilization, four days after reconstitution, and 14 days after reconstitution.

DETAILED DESCRIPTION

Figure 1:
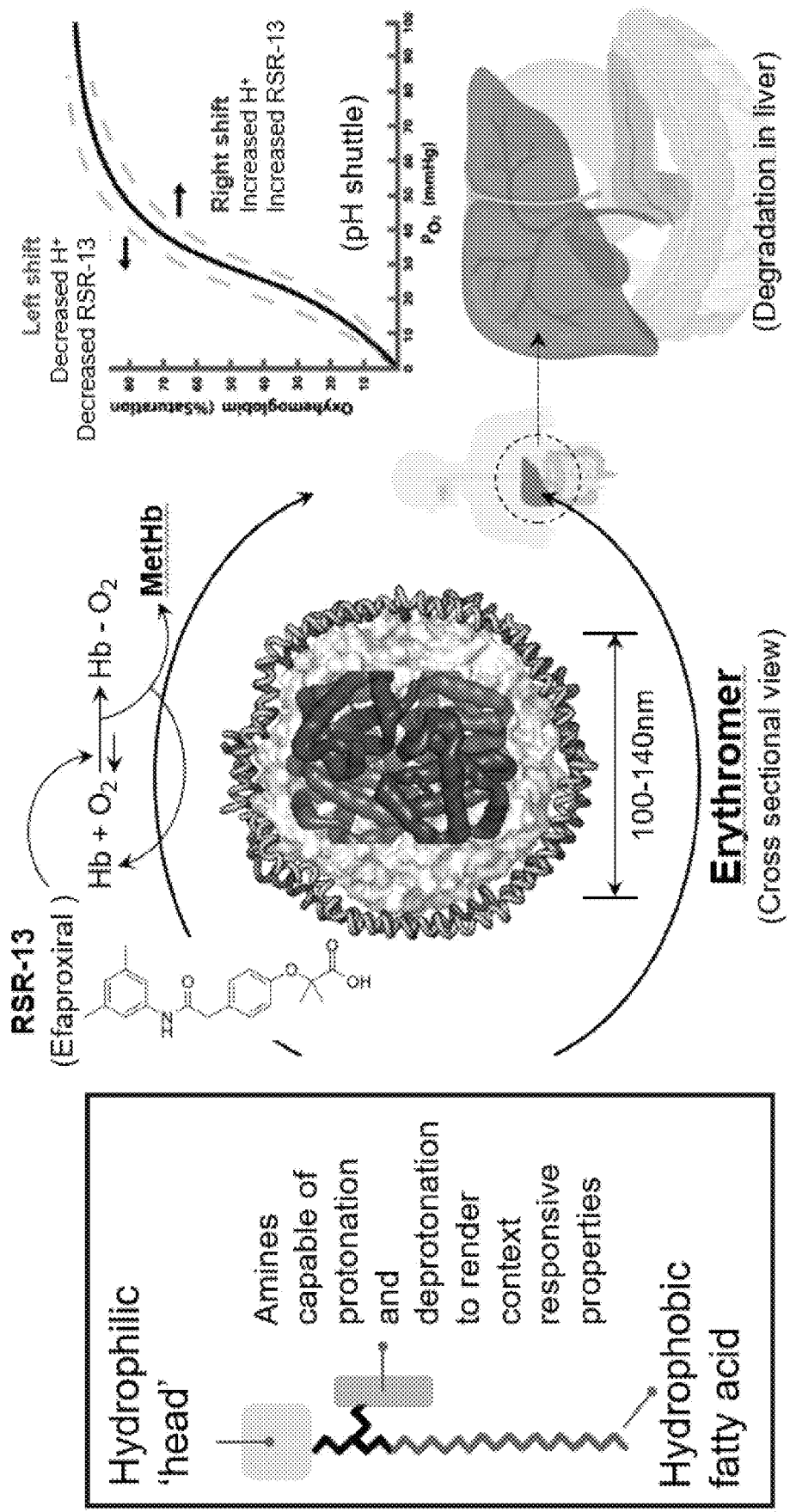
FIG. 1 is a schematic representation of the compositions and self-assembly according to an embodiment of the invention.
Figure 2:
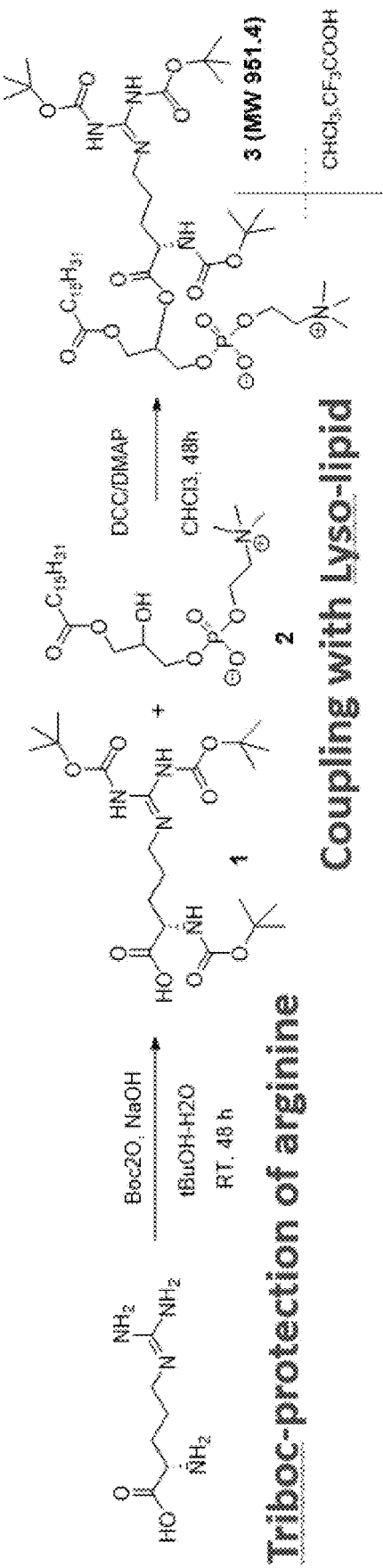
FIG. 2 is a representation of the synthesis of a precursor designated KC-1003 according to a preferred embodiment of the invention.
Figure 2:
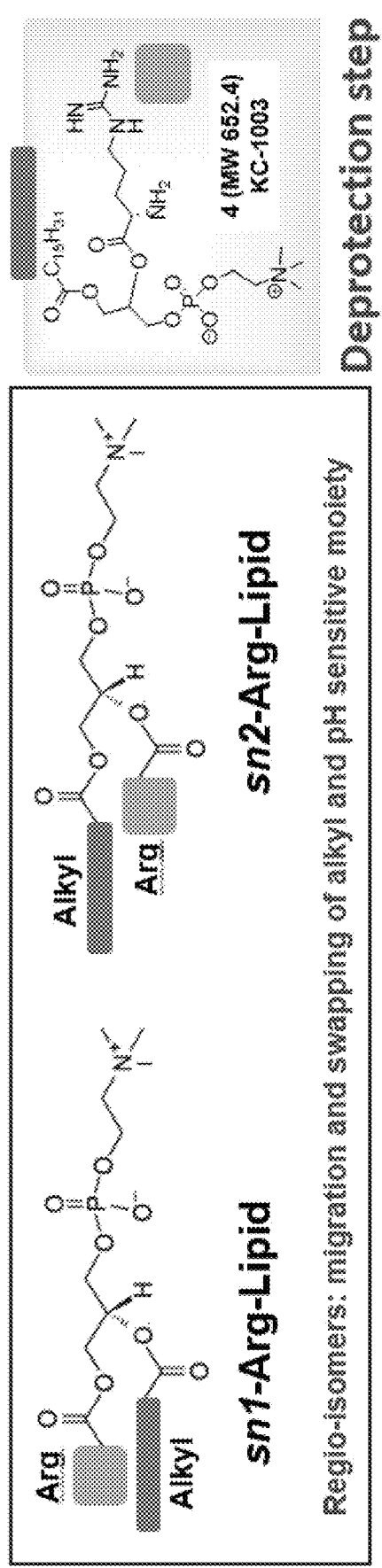
Figure 3:
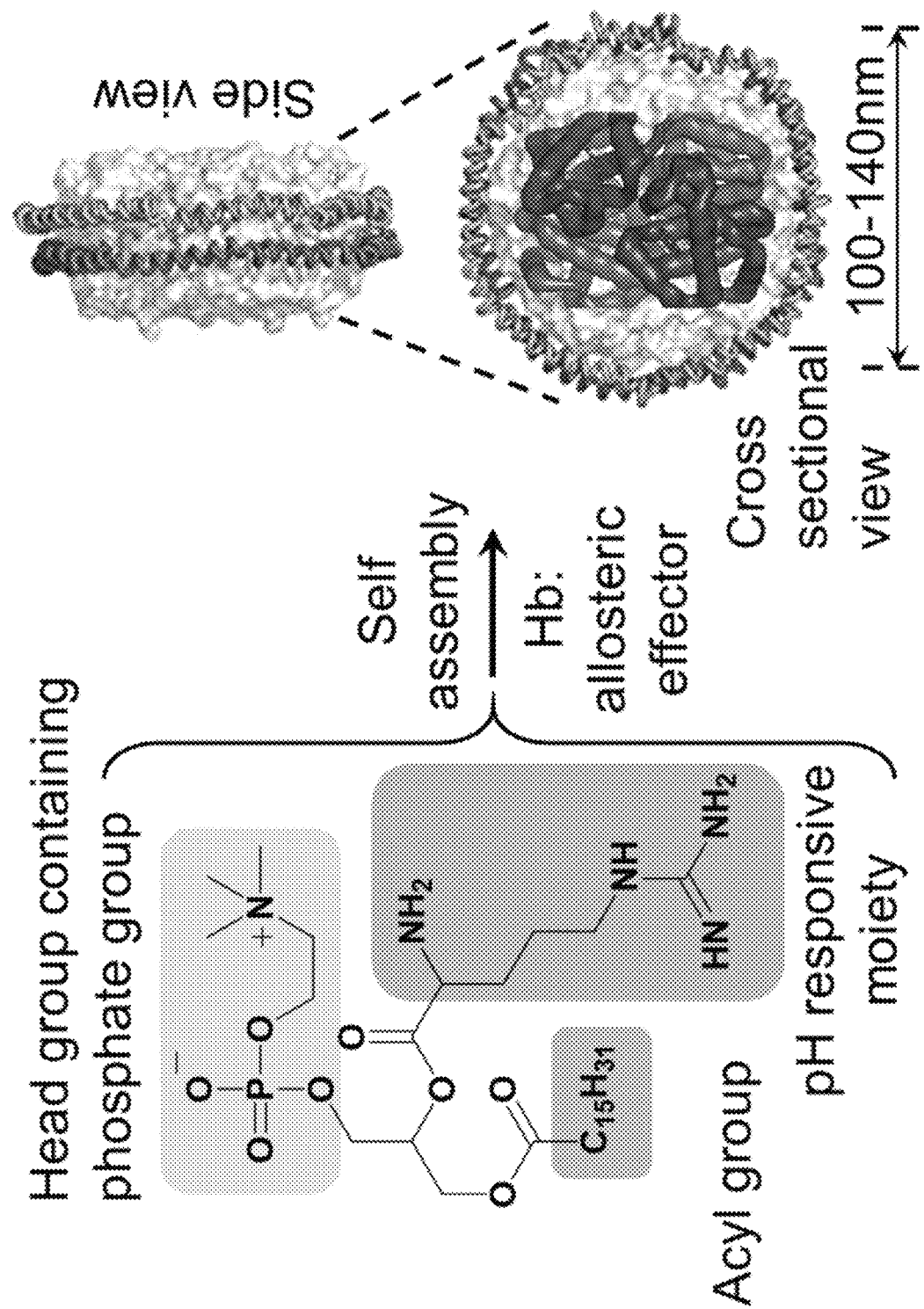
FIG. 3 is a schematic representation of the self-assembly of precursor KC-1003 and hb:allosteric effector into an oxygen carrier particle according to a preferred embodiment of the invention.
Figure 5:
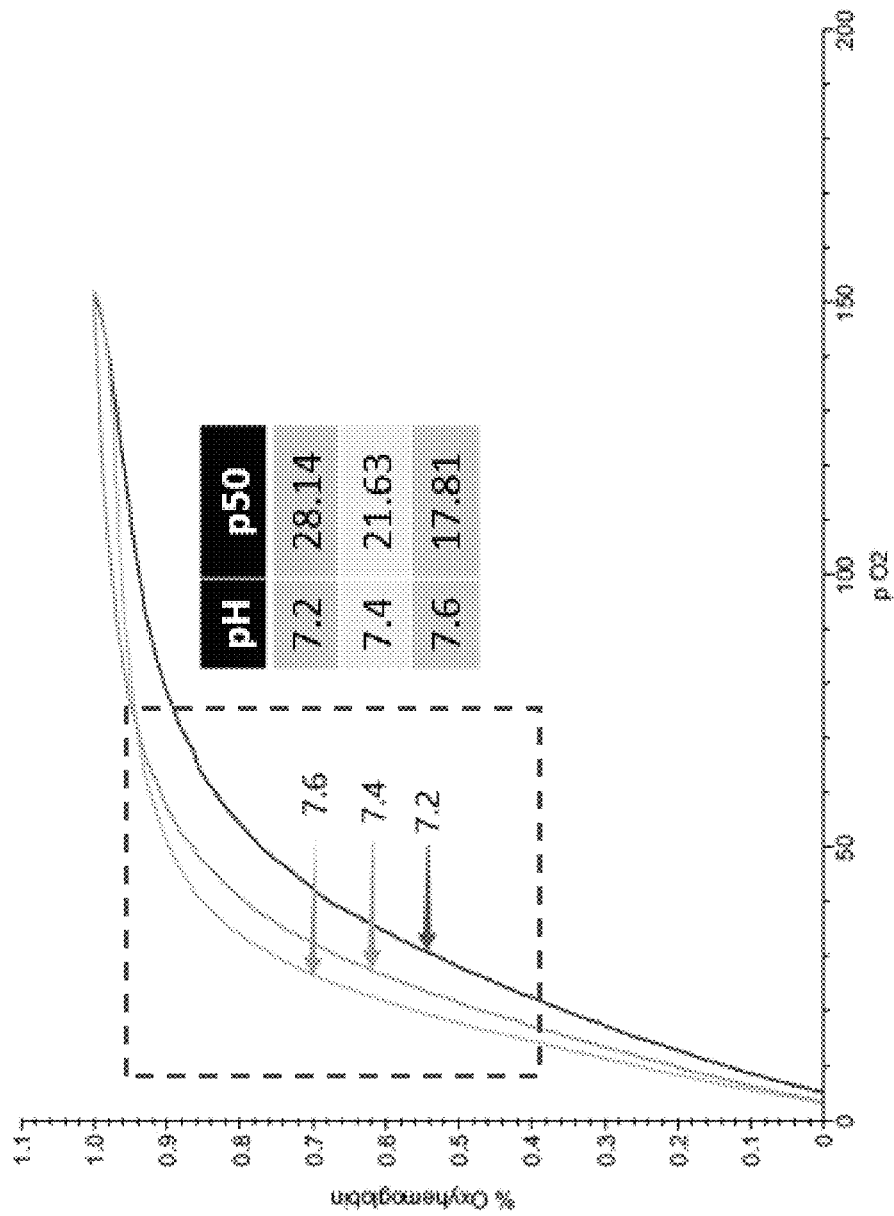
FIG. 5 is a chart showing the change in oxygen affinity with changes in pH for oxygen carrier particles according to the invention.
Figure 6:
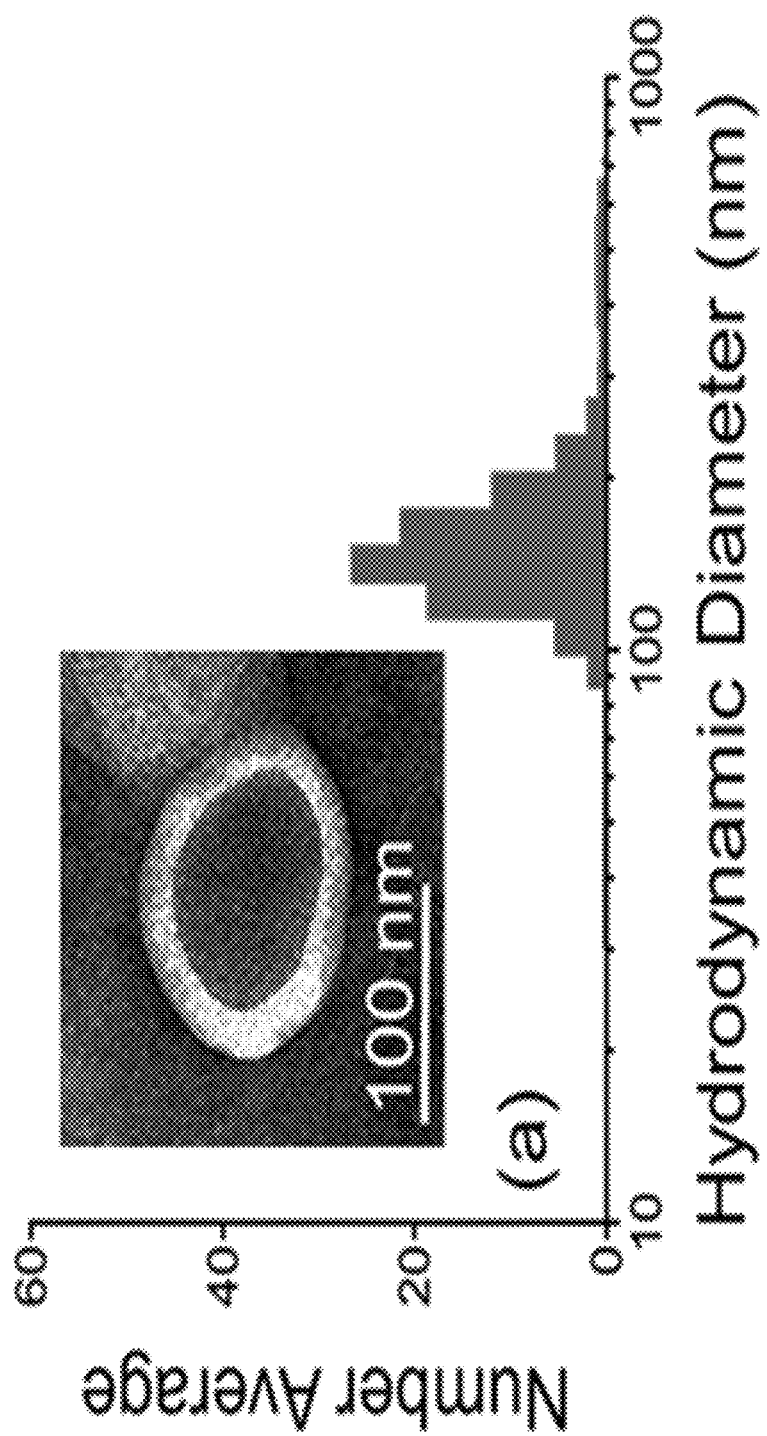
FIG. 6 shows the hydrodynamic diameter of a synthetic blood substitute and TEM image (inset) according to an embodiment of the invention.
Figure 7:
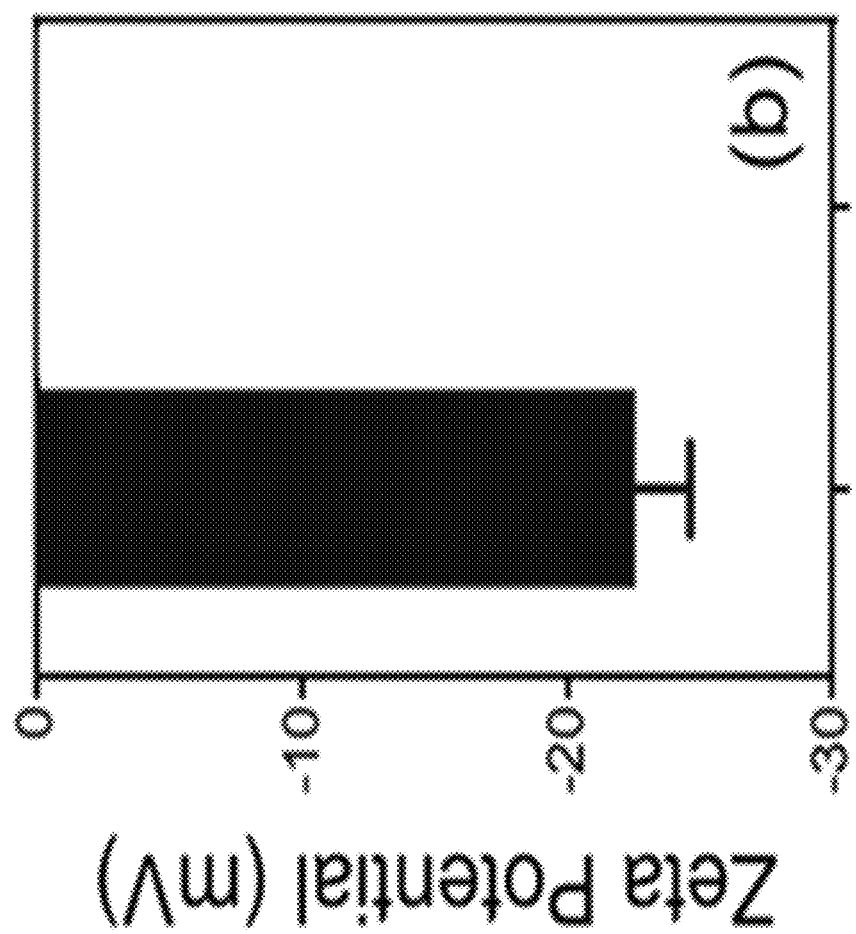
FIG. 7 shows the electrophoretic potential results according to an embodiment of the invention.
Figure 8:
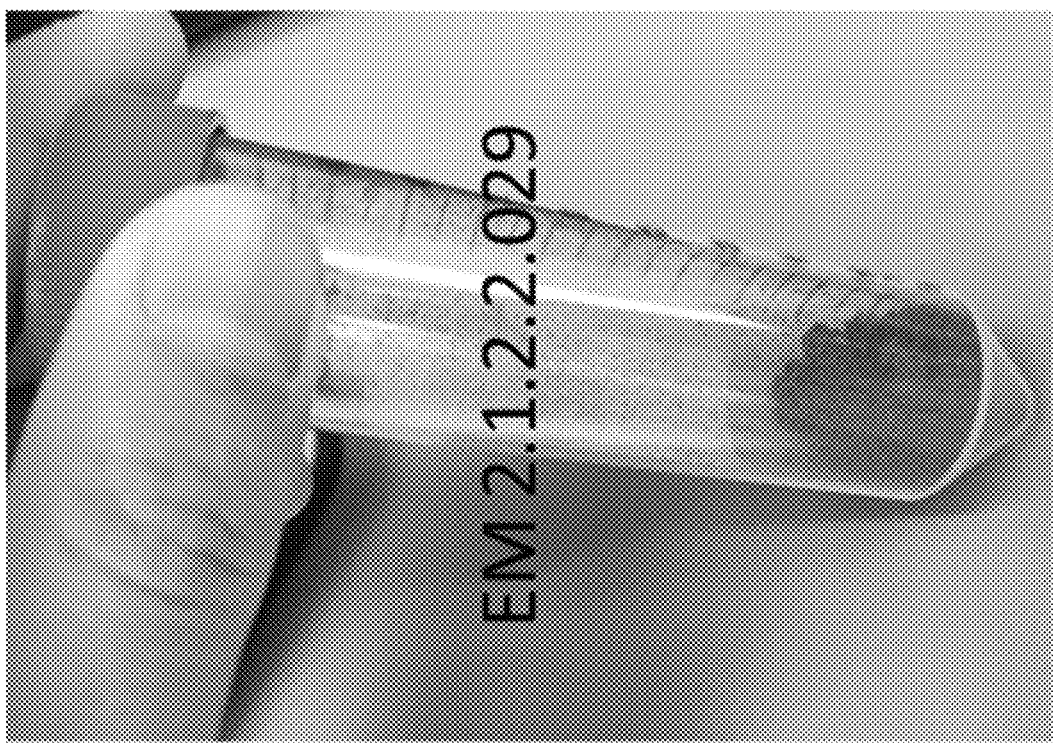
FIG. 8 shows a lyophilized sample of an oxygen carrier particle according to an embodiment of the invention.

Synthesis of preferred precursor KC-1003 is portrayed in FIG. 2. Lipid-oligomeric amphiphile is preferably synthesized and stored at 4° C. Purity of >90% may be confirmed by qHPLC, 1H NMR, 13C NMR and/or HRMS.

Precursor Film Preparation

1a. In the test tube (25×250 mm) precursor [KC 1003], [80.66 mmol] is dissolved in anhydrous chloroform to a concentration of [8 mg/mL]. Chloroform is transferred by glass syringe or measured by glass cylinder.

1b. [17 mmol] of cholesterol and [2.34 mmol] of [25 mg/mL][PEG2000-PE] are added to the test tube. Resulting in [100 mM] of surfactant in chloroform.

1c. The test tube is gently swirled for [1 min] to make homogenous/until solution is clear.

1d. Precursor solution is passed through a small bed of cotton to ensure no particulate presence.

1e. Chloroform is evaporated in the test tube under reduced pressure by rotary evaporator. Water bath temp is 50° C. Film is formed on the wall of the test tube and no more liquid chloroform is present.

1f. The test tube is dried in vacuum oven for [12 h], HV at room temperature, 20° C.

1g. The test tube is weighed again.

Self-Assembly

2a. Frozen hemoglobin at is placed at room temperature until melted, 20° C.

2b. Hemoglobin is transferred to 50 mL centrifuge tube by Eppendorf pipette and the lid is sealed immediately.

2c. Hemoglobin is transferred to the dried film in the test tube via micropipette to make a [6.339:1] of precursor to payload components Hb. The vessel is immediately sonicated (described in next step). Note: The same volume of stock Hb soln. to chloroform precursor mass is used.

Particle Size Normalization

3a. After mixing of payload and membrane components the test tube is immediately probe sonicated for [2 min for <5 mL, 5 min for >5 mL] in ice water. The test tube is swirled by hand on the stationary probe.

3b. After sonication, rest test tube for at least 15-20 min [actual time here] to achieve equilibrium from Brownian motion.

3c. Then, the hydrodynamic diameter is checked by DLS (nm and PDI).

Purification

4a. After sonication, the contents of the test tube are loaded on the Tangental Flow Filtration System and ran with a 50 nm PS membrane (D02-S05U-05-N) at a rate of 130 mL/min with lactated ringers.

4b. TFF is ran until the flow of outlet was clear by spectrophotometer.

4c. DLS (hydrodynamic diameter and PDI) are again checked and should be within 10% variance.

The resulting product is lyophilized for packaging. The lyophilized product is a powder comprising amphiphilic precursor, cholesterol and PEG-PE hemoglobin and allosteric effector, optionally also including cryoprotectants.

Reconstitution at the original EM production concentration (or concentrated) can be achieved with PBS/water by simple mixing and gentle vortexing/agitation.

The invention claimed is:

1. A composition comprising:
(a) a phospholipid,
(b) cholesterol,
(c) an oxygen carrier,
(d) a lipid-amphiphile precursor compound, and
(e) an allosteric effector,
the lipid-amphiphile precursor having the formula:

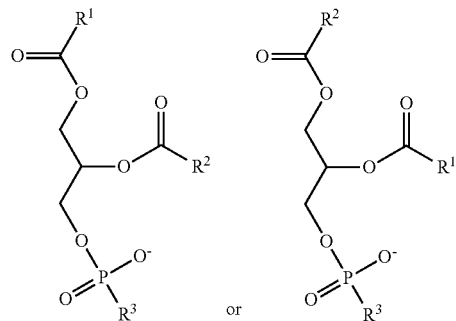

or a salt or tautomer thereof, wherein:

$R^1$ is a hydrophobic group, $R^2$ is

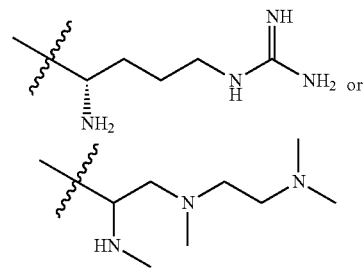

and $R^3$ is chosen from

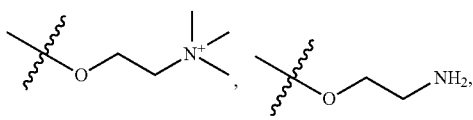

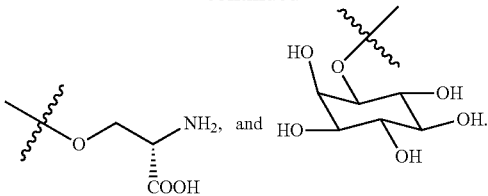

2. A composition according to claim 1, wherein the oxygen carrier is hemoglobin (Hb).

3. A composition according to claim 1, wherein the allosteric effector is selected from the group consisting of 2,3-DPG, RSR-13, inositol phosphate, inositol hexaphosphate (IP6), phytic acid, and guanosine triphosphate.

4. A composition according to claim 1, which self assembles into a vesicle having an amphiphilic lipid bi-layer membrane and a payload comprising said oxygen carrier and said allosteric effector.

5. A composition according to claim 1 further comprising a reducing agent.

6. A composition according to claim 5, wherein said reducing agent is selected from leucomethylene blue, n-benzoyl-leucomethylene blue, and methylene blue.

7. A composition according to claim 1, wherein $R^1$ is $(CH_2)_l CH_3$; and l is an integer between 10 and 16, inclusive.

8. A composition according to claim 1, wherein $R^3$ is

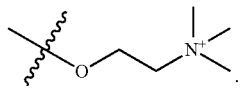 [SMILES: *OCC[N+](C)(C)C]

9. A composition according to claim 1, wherein $R^1$ is $(CH_2)_{14}CH_3$.

* * * * *